United States Patent
Kapps

(10) Patent No.: US 9,880,135 B2
(45) Date of Patent: Jan. 30, 2018

(54) AUTOMATICALLY CONTROLLING A PLURALITY OF DEVICES OF A SEPARATION AND DETECTION PROCESS FOR QUANTITATIVE SAMPLE ANALYSIS

(71) Applicant: Hoffmann-La Roche Inc., Nutley, NJ (US)

(72) Inventor: Martin Kapps, Magstatt-le_Haut (FR)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 920 days.

(21) Appl. No.: 13/919,125

(22) Filed: Jun. 17, 2013

(65) Prior Publication Data

US 2013/0303409 A1 Nov. 14, 2013

Related U.S. Application Data

(63) Continuation of application No. PCT/EP2011/070376, filed on Nov. 17, 2011.

(30) Foreign Application Priority Data

Dec. 17, 2010 (EP) .................................... 10195732

(51) Int. Cl.
G01N 30/02 (2006.01)
G01N 30/24 (2006.01)
G01N 30/86 (2006.01)

(52) U.S. Cl.
CPC ............. *G01N 30/02* (2013.01); *G01N 30/24* (2013.01); *G01N 30/8658* (2013.01)

(58) Field of Classification Search
CPC ..... G01N 30/24; G01N 30/02; G01N 30/8658
See application file for complete search history.

(56) References Cited

U.S. PATENT DOCUMENTS

| | | | |
|---|---|---|---|
| 5,585,070 A | 12/1996 | Lessard et al. | |
| 5,658,800 A | 8/1997 | Lessard et al. | |
| 6,456,955 B1 | 9/2002 | Andrews et al. | |
| 6,895,364 B2 | 5/2005 | Banfer | |
| 7,566,395 B2 | 7/2009 | Lundblad et al. | |
| 2002/0107652 A1 | 8/2002 | Andrews et al. | |

(Continued)

FOREIGN PATENT DOCUMENTS

| | | |
|---|---|---|
| CN | 1517711 A | 8/2004 |
| CN | 1815219 A | 8/2006 |

(Continued)

OTHER PUBLICATIONS

Anderson, N. G. et al. (May 26, 1975). "Analytical Techniques for Cell Fractions: XIX. The Cyclum: An Automatic System for Cyclic Chromatography," *Anal. Biochem.* 66(1):159-174.

(Continued)

*Primary Examiner* — Shogo Sasaki
(74) *Attorney, Agent, or Firm* — Morrison & Foerster LLP

(57) ABSTRACT

A control system (1) for automatically controlling a plurality of devices (2) of a separation and detection process for quantitative sample analysis and according computer program. Such systems and computer programs can be used to operate quantitative sample analysis devices such as for example high performance liquid chromatography (HPLC) devices or the like.

17 Claims, 2 Drawing Sheets

(56) References Cited

U.S. PATENT DOCUMENTS

| | | |
|---|---|---|
| 2004/0158433 A1 | 8/2004 | Wimschneider et al. |
| 2006/0005640 A1 | 1/2006 | Osaka |
| 2006/0207941 A1 | 9/2006 | Morikawa |
| 2007/0059207 A1 | 3/2007 | Lin et al. |
| 2007/0213939 A1* | 9/2007 | Liew .................... C12Q 1/6886 702/20 |
| 2008/0142444 A1 | 6/2008 | Toyosaki |

FOREIGN PATENT DOCUMENTS

| | | |
|---|---|---|
| CN | 1890561 A | 1/2007 |
| CN | 101191790 A | 6/2008 |
| JP | 2004-507749 A | 3/2004 |
| JP | 2004-515770 A | 5/2004 |
| JP | 2004-226402 A | 8/2004 |
| JP | 2005-003455 A | 1/2005 |
| JP | 2007-040858 A | 2/2007 |
| WO | 2005/025713 | 3/2005 |

OTHER PUBLICATIONS

Wajcman, H. et al. (Feb. 15, 1979). "Quantitation of Hemoglobin A1c: A Rapid, Automated Precision-Chromatography Technique," *Clin. Chim. Acta*. 92(1):33-39.

* cited by examiner

AUTOMATICALLY CONTROLLING A PLURALITY OF DEVICES OF A SEPARATION AND DETECTION PROCESS FOR QUANTITATIVE SAMPLE ANALYSIS

This application is a continuation of International Patent Application No. PCT/EP2011/070376, filed Nov. 17, 2011, the content of each of which hereby incorporated herein by reference in its entirety, and which claims priority benefit to EP 10195732.2 filed Dec. 17, 2010.

TECHNICAL FIELD

The present invention relates to a control system for automatically controlling a plurality of devices of a separation and detection process for quantitative sample analysis and an according computer program. Such systems and computer programs can be used to operate quantitative sample analysis devices such as for example high performance liquid chromatography (HPLC) devices or the like.

BACKGROUND ART

In today's quantitative sample analysis often separation and detection processes are involved wherein for that purpose a variety appropriate devices or combinations of devices are commonly used. For example, within quantitative sample analysis applying high performance liquid chromatography (HPLC) devices for separation and detection such as pumps, autosamplers, injectors, columns, valves and detectors are commonly used. Often, such devices are controllable via a control software being executed on a computer as control system. Usually, a plurality of such devices is combined to an analytical instrument allowing to perform the separation and detection processes of the quantitative sample analysis. Some combinations of these devices or analytical instruments can also be controlled by one single control software being executed on a computer. Such controlling of a whole analytical instrument by a single control system can provide a convenient and efficient handling of the analytical instrument.

However, often such analytical instruments are not perfectly suitable to the needs of a specific sample analysis or to a flexible arrangement of sample analyses for example in a laboratory. In such laboratories, for example taking care of high throughput analytics of a company of the pharmaceutical industry, huge numbers of compounds and samples can be quantified per year such as, e.g., about 5'000 compounds in about 250'000 samples. Thereby, the compounds can, e.g., be small molecules having a molar weight between about 100 g per Mol to about 700 g per Mol.

Within this frame efficient analytical instruments and tools to support the analytical method development, the routine analytics, instrument management, reporting and many other tasks can be of crucial importance. Therefore, a rearrangement of the devices of an analytical instrument or a free combination of devices from different suppliers for assembling a suitable instrument is often desired. In that case, the provided convenient control of the analytical instrument via one single control system or part of the functionalities of the single control system is usually at least partially lost. Furthermore, such single control systems often do not fully support all functionalities and operations of an analytical instrument or of certain devices thereof. For example, laboratory activities like method development, preventive maintenance, sample preparation and the like are often not supported by such single control systems. Thus, a comparably inefficient operation of the analytical instrument can result, e.g., particularly including a comparably low utilization rate of at least some of the devices. Additionally, such single control systems are usually not standardized and can therefore not be fully customizable and integratable in, e.g., a commercially available or other laboratory information management system (LIMS) which are mainly focusing on sample workflow, result workflow and data evaluation tools and not covering other laboratory activities.

Therefore, there is a need for a preferably automatic control of a plurality of devices of a separation and detection process allowing an efficient quantitative sample analysis particularly suitable for comparably large numbers of analysis per time unit.

DISCLOSURE OF THE INVENTION

According to the invention this need is settled by a control system as it is defined by the features of independent claim 1, and by a computer program. Preferred embodiments are subject of the dependent claims.

The gist of the invention is: A control system for automatically controlling a plurality of devices of a separation and detection process for quantitative sample analysis, comprises a data storage, a device modelling unit, a sample modelling unit, a sequence generating unit and an interface unit. Thereby, the data storage is arranged to hold characteristic data of each of the devices and the device modelling unit is arranged to model the devices using the characteristic data of the devices held in the data storage. Further, the data storage is arranged to hold data of source samples and the sample modelling unit is arranged to generate a plurality of analytical samples to be analysed in the separation and detection process for quantitative sample analysis using the data of source samples held in the data storage. The sequence generating unit is arranged to define an analytical sample sequence of the analytical samples within the separation and detection process for quantitative sample analysis taking into account utilization of the devices. Still further, the interface unit is arranged to operate the devices of the separation and detection process for quantitative sample analysis in accordance with the analytical sample sequence defined by the sequence generating unit.

The control system can particularly be a conventional computer having a central processing unit (CPU) or processor, a random access memory (RAM) and a hard disk, on which computer a computer program is executed in order to implement the data storage and the units described above. In the context of the present invention, the term "separation and detection process for quantitative sample analysis" can particularly relate to chromatographic processes such as high performance liquid chromatography (HPLC) processes, ultra high performance liquid chromatography (UPLC) processes, gas chromatography (GC) processes, to electrophoresis processes, or to similar processes. The devices of such a process can particularly comprise a pump, a detector such as a ultraviolet-visible (UV/VIS) spectroscopy detector, an evaporative light scattering detector (ELSD), a refractive index detector, a mass spectrometry (MS) detector, a conductivity detector, a electrochemical detector, a radioactivity detector, a fluorescence detector or a nitrogen selective detector, an injector and the like. The data storage, e.g., can be any kind of computer data storage such as one or more databases with or without database management system, a flat file repository, combinations thereof or the like. In this context, the characteristic data of the devices relates to parameters of the devices characteristic for operation. Such characteristic data can comprise volume, pressure, temperature, capacity, flow and the like. Modelling the devices within the device modelling unit can comprise reproducing each of the devices according to their characteristic data and establishing the interactions between the devices within the separation and detection process for quantitative sample analysis. Furthermore, modelling the devices can comprise combining a plurality of devices into an analytical instrument.

The data of source samples can be manually inputted into the control system or, in particular, imported from a laboratory information management system (LIMS) or from import templates. In the context of the invention, the term "generating analytical samples" relates to adjusting raw imported sample data held in the data storage or parameters in accordance with a specific analytical run to be performed within the separation and detection process for quantitative sample analysis. In particular, such adjustment can comprise applying a dilution factor, calculating the average concentration if one of the samples is processed several times or the like.

Utilization of the devices can relate to utilization by time such that taking into account said utilization can relate to a preferred use of the devices over time. Thereby, optimized utilization can relate to utilization of the devices heading for an efficient use of the devices with regard to process time, process costs, sample throughput, quality of the analysis results and the like. By taking into account utilization of the devices for generating the analytical sample sequence said utilization and also the separation and detection process for quantitative sample analysis can be optimized. It particularly allows for coordinating and synchronizing the devices such that an efficient separation and detection process for quantitative sample analysis results. Thus, the sequence generating unit can particularly be arranged to adjust the parameters relating to the optimized utilization of the devices thereby allowing for an efficient separation and detection process for quantitative sample analysis and in particular a HPLC-process. Furthermore, it allows integrally controlling and performing the separation and detection process for quantitative sample analysis wherein various tasks are centrally organised and initiated.

Preferably, the control system comprises a method modelling unit wherein the data storage is arranged to hold data of methods for the separation and detection process for quantitative sample analysis, the method modelling unit is arranged to provide an appropriate method for the separation and detection process for quantitative sample analysis in accordance with the analytical sample sequence defined by the sequence generating unit using the methods data held in the data storage, and the interface unit is arranged to operate the devices of the separation and detection process for quantitative sample analysis in accordance with the appropriate method provided by the method modelling unit. Appropriate method in this context relates to a method particularly suitable for an efficient separation and detection process for quantitative sample analysis depending, e.g. on the involved samples, instruments, conditions, sequence and the like. It can relate to adjustment of parameters of the devices allowing the compounds or samples, respectively, to be processed within the high performance liquid chromatography process. Particularly, it can relate to parameters relating to detection such as mass spectrometry trace with declustering potential (DP) and collision energy (CE), ultra violet wavelength and the like, to chromatography such as column, mobile phase, gradient and the like, to compound information such as molecular weight (MW), name, project and the like and/or to method information such as status, sensitivity and the like. Appropriate method, e.g., as a combination of separation and detection conditions, in this context can relate to a combination and operation of the devices particularly taking into account the separation conditions of the sample and the detection conditions of the compound. By means of such a method modelling unit, one or more appropriate methods can automatically be provided by the control system and the appropriate method can, e.g., be chosen by an operator of the control system. Therein, the data storage preferably is arranged to hold data of compounds of the source samples and the method modelling unit is arranged to evaluate the appropriate method within the separation and detection process for quantitative sample analysis for each of the compounds of the source sample. Thereby, the method modelling unit preferably is arranged to provide a presentation of appropriate methods and to detect a selection of the appropriate method. The presentation can be a graphical user interface showing a list of the appropriate methods. The input can be detected by a click signal, by analysing an input text, by analysing a pressing of a key or the like. Further, the method modelling unit preferably is arranged to evaluate a failed method within the separation and detection process for quantitative sample analysis for the compounds of the source sample. Such an arrangement can allow for a particularly convenient and efficient method selection.

Preferably, the control system holds interface format data of control software of at least one of the devices wherein the interface unit is arranged to communicate with the control software of the at least one of the devices in order to operate the at least one of the devices within the separation and detection process for quantitative sample analysis in accordance with the analytical sample sequence defined by the sequence generating unit using the interface format data. The control software, e.g., can be a computer program, a plurality of computer programs or a combination of computer program(s) and associated data. In this context, interface format data relates to data or meta data defining a format of an interface allowing interaction with the at least one of the devices. For example, it can relate to the structure and content of a character separated values (CSV) file which is intended to be exchanged between the control system and the at least one of the devices. Holding the interface format data can be established by arranging the data storage to hold the interface format data of the native software of each of the devices. Control software in this context relates to native software of the devices used to control the devices. Particularly, at least one of the devices can be all of the devices of the separation and detection process for quantitative sample analysis as mentioned above, i.e. all devices of the analytical instrument. Such an arrangement of the control system allows for a comparably easy implementation of the interface unit and for an efficient data exchange. Thereby, the interface unit preferably is arranged to communicate with the control software of the at least one of the devices by generating files which are importable by the control software of the at least one of the devices. Files in this context can particularly be digital text files such as computer readable files having text represented by a character-encoding scheme such as, e.g., the American Standard Code for Information Interchange (ASCII) or Unicode.

Preferably, the control system comprises a robot unit being arranged to control a robot to transform a plurality of source samples located in source sample containers into the analytical samples generated by the sample modelling unit and located in processing sample containers in accordance with the analytical sample sequence defined by the sequence generating unit. In this context, sample containers relate to containers such as tubes or well plates suitable for handling the samples. Thereby, well plates can be, e.g., multi-well microplates which are standardized and commonly used for storage and/or transportation of samples. For example, such standards developed by the Society for Biomolecular Screening (SBS) and approved by the American National Standards Institute (ANSI) define microplates of 127.76 mm length, 85.48 mm width and 14.35 mm height comprising 96, 384 or 1536 wells [see Society for Biomolecular Screening. ANSI/SBS 1-2004: Microplates—Footprint Dimensions, ANSI/SBS 2-2004: Microplates—Height Dimensions, ANSI/SBS 3-2004: Microplates—Bottom Outside Flange Dimensions and ANSI/SBS 4-2004: Microplates—Well Positions. http://www.sbsonline.org: Society for Biomolecular Screening, 2004.] The plurality of source samples can be a selection of the source samples held in the data storage and can correspond to physical samples delivered in order to be analysed within the high performance liquid chromatography process. The robot can be, e.g., a pipetting robot such as the pipetting robots of the company Tecan Group Ltd. marked with the term "Genesis" or "Evo" which are widely known in the art. The data of the source samples delivered in the source well plates can comprise plate names or plate identifications, respectively, well identifications, compound to be analysed and the like. Analytical samples relates in this context to samples being prepared for the analysis within the separation and detection process for quantitative sample analysis and being arranged in the processing well plates by the robot controlled by the control unit of the control system. Such an arrangement of the control system can allow for an efficient sample handling in particular in cases where comparably large amounts of samples are involved such as in a laboratory.

Thereby, the robot unit preferably is arranged to apply volume transfer within transformation of the source samples into the analytical samples. Volume transfer in this context relates to a sample preparation step involving an activity resulting in a transfer of volume within the samples. In particular, volume transfer can comprise dilution of samples, removal of proteins from samples, e.g., by precipitation, calibration samples preparation and the like. Further, thereby the control system preferably holds robot interface format data of control software of the robot wherein the interface unit is arranged to communicate with the control software of the robot in order to operate the robot for transforming the source samples located in the source sample containers into the analytical samples located in the processing sample containers. In an exemplary use of the control system, a user of the control system imports source sample information into the control system which virtually creates the analytical sample and exports text files for the pipetting robot, puts the physical source samples and empty processing plates on the robot, launches the robot and the robot prepares the analytical samples according to virtual preparation of the control system.

Preferably, the devices of the separation and detection process for quantitative sample analysis comprise a first number of separation devices, a second number of injection devices and a third number of detection devices, wherein at least one of the first number, the second number and the third number is bigger than another one of the first number, the second number and the third number, and wherein the sequence generating unit is arranged to define the analytical sample sequence such that the devices of bigger number alternatingly interoperate with the devices of smaller number. Processing samples by such multi lines separation and detection process for quantitative sample analysis and in particular multi lines HPLC being commonly known as multiplexing HPLC, allows for increasing the utilization of the detector device. Since the detector device is usually the most expensive of the devices used within HPLC-processes, such multiplexing can increase the overall efficiency. Thereby, the first number and the second number preferably can be equal and are bigger than the third number wherein the separation devices and the injection devices are arranged in a plurality of lines being connected to the at least one detector device. In other words, the sequence generating unit can be arranged to define the analytical sample sequence such that the lines alternatingly provide a sample to the detector device when being applied. Like this, the detector unit can efficiently be used and its utilization can be increased which can be particularly important in processes such as HPLC processes using a mass spectrometer as detector, in which the detector device is the most expensive but often faster device.

Preferably, the data of source samples comprise compound data and the sample modelling unit is arranged to evaluate the compound data of the source samples with regard to their detection trace and with regard to the compatibility of their chromatographic preferences and to mix suitable source samples when generating the plurality of analytical samples to be analysed in the separation and detection process for quantitative sample analysis. In this context, detection trace relates to the output graph generated by the detector device wherein the graph of each compound usually has a specific peak at a specific location. Further, chromatographic preferences relates for example to preferences such as process temperature, process pressure and the like. Suitable source samples relate to compatibility with regard to the chromatographic preferences and to identifiability of the output graph comprising peaks of each of the source samples. Processing samples by such sample mixture HPLC, which is commonly known as sample cocktail analytics, allows for increasing the efficiency of the HPLC process.

Preferably, the control system comprises a maintenance unit wherein the data storage is arranged to hold data of each of the devices and the maintenance unit is arranged to induce maintenance of the devices taking into account the data of each of the devices. The term "induce device maintenance" in this context relates to various maintenance actions such as triggering preventive device maintenance after a certain use of the according device, storing and displaying device events such as successful runs, errors, repairings and the like, defining default parameters of the devices, displaying device inventories, estimating costs of analytical runs with regard to the devices and the like. Like this, an efficient and convenient maintenance of the devices is possible. Thereby, the maintenance unit preferably is arranged to predefine a value of maintenance data of each of the devices, to count a trigger value associated to the maintenance data of each of the devices and to provide an alert when the counted trigger value equals the predefined value. The value for maintenance data of each of the devices can be predefined by, e.g., inputting the value into the control system. In particular, a set of values can be inputted by a maintenance plan wherein maintenance plan in this context relates to one or more maintenance events associated to a specific trigger value. For example, maintenance events can be cleaning the device, replacing certain parts of the device or the like. Trigger value in this context relates to an action performed with the according device such as, e.g., an injection performed by the device, a calendar day, a used solvent volume or the like. Providing an alert can be provided by requesting a specific maintenance event and it can include blocking the associated device until the maintenance event is performed. Further, the maintenance unit preferably is arranged to store data of maintenance of each of the devices in the data storage and to provide a maintenance report for each of the devices.

Preferably, the characteristic data of each of the devices comprise default settings of each of the devices and the sequence generating unit is arranged to define the analytical sample sequence of the analytical samples in accordance with the default settings of each of the devices. Default settings in this context relate to settings specific to one of the devices and specific to the intended run. They can particularly comprise a type of injection method, a file system pathway for storing data or a text file, an injection volume and the like.

A further aspect of the invention relates to a computer program comprising program code arranged to be executed to implement the system described above. Such a computer program allows for an easy implementation of the system according to invention thereby achieving the corresponding advantageous effects.

These and other aspects of the invention will be apparent from and elucidated with reference to the embodiment(s) described hereinafter.

BRIEF DESCRIPTION OF THE DRAWINGS

The control system and the computer program according to the invention are described in more detail hereinbelow by way of an exemplary embodiment and with reference to the attached drawings, in which.

MODE(S) FOR CARRYING OUT THE INVENTION

Figure 1:
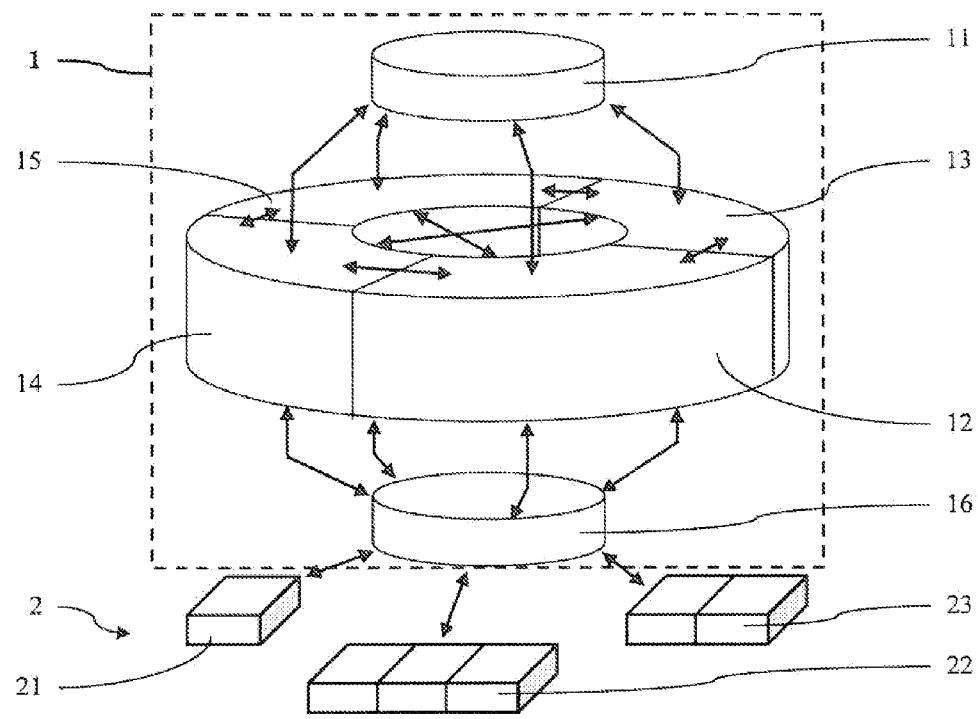
FIG. 1 shows a schematic view of the components of an embodiment of a control system according to the invention.

In FIG. 1 a software or computer program according to the invention executed on a computer and thereby implementing a control system 1 according to the invention for automatically controlling a plurality of devices 2 of a high performance liquid chromatography process (HPLC-process) as a separation and detection process for quantitative sample analysis is shown. The control system 1 comprises a data storage 11 and an interface unit 16 as well as various modules which can be used alone or in combination in order to create synergies. The modules can be implemented as separate applications on the computer or as parts of a single applications. The modules comprise a device modelling unit 12, a sample modelling unit 13, a sequence generating unit 14 and a method modelling unit 15. As indicated by the corresponding arrows, the interface unit 16 is arranged to interact with each of a combination of devices 2 forming an analytical instrument for a HPLC-process. The analytical instrument comprise an injection device 21, a separation device 22 and a detector device 23.

The control system 1 is arranged as a tool to perform a complete analytical run of the HPLC analysis process. It allows the coordination and synchronization from the devices 2 which are part of the analytical HPLC instrument. The data storage 11 is arranged to hold and import data of source samples to analyze which, e.g., can be provided by a laboratory information system (LIMS) or from an import template. It further holds characteristic data of the devices 2 of the analytical instrument. The analytical samples are then generated electronically as they are prepared physically by a human analyst or user in the laboratory. Such generation comprises transfer of the source sample to analyze to a new sample container, sample dilution, calibrator and quality control. Considering the data of the samples as well as of the devices 2, the sequence generating unit 15 defines an analytical sample sequence such as an injection order of the samples taking into account efficient utilization of the devices 2. Each sample is linked to the required analytical parameters, like injection method, mobile phase, gradient profile, detection method and the like. As shown in more detail below, the control system 1 further comprises optional procedures to manipulate the analytical sample sequence for multiplexing or sample cocktail analysis.

For interacting with the devices 2, the interface unit 16 generates text files called work lists of a predefined format. Those work lists are imported into native software of the devices 2 and used to control the native software corresponding to the devices 2. By using the native software within device control, access to the whole panel of functionalities of the devices 2 can be obtained.

The source sample and devices 2 raw data of an analytical run can be imported to the control system 1. During the import dilution factor is applied and, if a sample is injected several times, the average concentration is calculated by the control system 1. When the data from the analytical run are accepted (or validated by the user) any modification of the data is blocked and reports can be created and/or exported by the control system 1. The control system 1 allows to analyze samples and to deliver the results with the appropriate quality and within comparably short time.

The method modelling unit 15 is used to support the analytical method development and to store the analytical method parameters in the data storage 11. For example, a list of compounds to be analyzed is imported to an optimization batch. By querying the data storage 11 existing methods can be found and provided by the method modelling unit 15. An operating person or analyst or user can then decide according to the information linked to the found methods if he wants to use them like they are or if he wants to redevelop or adapt them. Further, the method modelling unit 15 allows for manual development (compound by compound) and automated development using an according software such as the software of the company AB Sciex marked as "DiscoveryQuant". The method modelling unit 15 presents the finalized methods for search purposes. The parameters of such analytical method are covering the detection such as mass spectrometry trace with declustering potential (DP) and collision energy (CE), ultra violet wavelength or the like, chromatography such as column, mobile phase, gradient or the like, compound information such as molecular weight (MW), name, project or the like and method information such as status, sensitivity or the like.

The method modelling unit 15 also has failure recognition and evaluation. According to the number of compounds for which methods are developed within the control system 1 cases are present where method development failed due to different reasons such as, e.g., compound not being stable, compound not being pure enough or the like. Thereby, a possibility to flag compounds and to store information about the reason of the failure such as comments or screenshot pictures from chromatograms, spectra or the like is provided. If a flagged compound is resubmitted for analytics then the method modelling unit 15 informs about the potential problems with this compound.

The interface unit 16 supports data processing such as chromatogram integration. Native software of the devices 2 such as delivered with the detector 23 or mass spectrometer is designed to process raw data analyte by analyte. The interface unit 16 controls the native software from the detector 23 and other devices 2 using an exported work list as input file where analyte name and trace, internal standard name and trace, chromatogram filename and file location are defined. The input work list is generated by the interface unit 16 accessing information from the data storage 11.

The control system 1 allows looped or iterative creation of methods needed for the data processing, processing the data and formatting the final data.

The device modelling unit 12 is arranged to define analytical instruments by combining a plurality of devices 2. It is used to store and retrieve all necessary type of data related to the devices 2 and the analytical instruments as well as associated devices used or stored in the laboratory. Further, the device modelling unit 12 or a maintenance unit is arranged to trigger a preventive maintenance, to store all events related to the devices 2 (logbook functionalities), to define the analytical instrument work lines with default parameters such as methods, file and folder pathway or the like, to give a real time inventory of the used or non used of the devices 2 and to perform cost estimation linked to instrumentation such as purchasing, maintenance, repair or the like.

In the device modelling unit 12 following basics are defined: A device is the smallest and non divisible part such as a pump, a column, an injection valve, a detector or the like. A device can be used as a stand alone tool or in combination with other devices. A device module is a combination of one to more devices which usually are used together such as a gradient pump, as a device module being composed of an aqueous pump, an organic pump, and a pump controller or as a column module being composed of a analytical column, a pre-column and a column oven. A work line is a combination of one or more modules needed to perform a job such a, e.g., a work line on a liquid chromatography-mass spectrometry system can be composed by the device modules gradient pump, injector, column and detector. One device module can be used on different work lines which is particularly the case for multiplexing where chromatography is performed on different pump and column modules but the same detector module is used on the different work lines. A configuration is used to link one or more work lines which can be used simultaneously on an analytical instrument. The analytical instrument can have one or more configurations. A laboratory is the highest hierarchical level to link instruments which belong together.

The control system 1 further comprises the maintenance unit for associating a maintenance plan to the devices 2. Thereby, the maintenance plan is composed by one or more maintenance events which can be induced by the maintenance unit. A maintenance event is defined by an action to perform in association with a trigger. The trigger or trigger value can be an injection count performed on the device, calendar days, used solvent volume or the like. A trigger value counter can be automatically updated by the control system 1 when an analysis is performed. As soon as the trigger value counter reaches the set trigger value, the maintenance unit requests to perform the corresponding maintenance event. When the maintenance event is performed the trigger value counter is reset by and a new cycle starts. The maintenance unit is further arranged to log maintenance events and to provide a maintenance report. In particular, different maintenance events and information is automatically linked to the devices 2 like the performed preventive maintenance (PM) event information, non planned services done by the user himself or done by an external company, as well as trigger data from the preventive maintenance and the like.

In the device modelling unit 12 different data can be linked to the work line. Those data can be used as default parameters for the work line such as injection method, folder pathway for the raw data, injection volume or the like, and can be accessed directly from control system 1. To analyze a sample it is then only needed to select the work line on which the sample should be analyzed and all the default parameter are then provided by the device modelling unit 12. Thereby, data like column name, mobile phase, different method used is also used to generate the method description in an analytical report.

The sample modelling unit 13 allows preparing the analytical samples by using a pipetting robot like a Tecan Genesis. The source samples are obtained, e.g. from laboratory customers and are delivered in tubes or on 96 or 384 multiwell microplates or well plates as sample container. The information about the source samples like plate name, well name, and compound to analyze and the like are imported into the data storage 11. Analytical samples are samples prepared by the sample modelling unit using the source samples and injected on the analytical instruments. In some cases, the source samples are prepared such as diluted, proteins are removed by precipitation, calibration samples are prepared and the like. All those activities are mainly volume transfer steps from the source samples located in source well plates to the analytical samples including or not addition of liquid reagent located in processing well plates.

The sample modelling unit 13 virtually prepares the analytical samples. The automatic sample modelling unit 13 comprises a robot unit generating a work list readable by the pipetting robot and containing all pipetting steps information from source sample container to processing sample container with the volumes to transfer. In summary, the user imports the source sample information into the control system 1, the sample modelling unit 13 of which virtually creates the analytical sample, exports the work list for the pipetting robot, puts the physical source samples and the empty processing sample container on the robot, launches the robot and the analytical samples are prepared according to the virtual preparation.

The control system 1 further comprises a statistic unit updating the data storage 11 every time when a work list is exported from the control system to the analytical instruments or when an analysis is finalized the data storage is updated automatically. The stored information, e.g., comprises experiment identifier, number of samples analyzed, date, instrument identifier and the like. By the statistic unit querying the data storage 11, real time information about workload and analysis performed by quarter or by year can be obtained. Like this, it is possible to evaluate the effective cost per analyzed sample or to identify strengths or weaknesses of the laboratory.

The control system 1 further comprises a diagnostic tool to identify technical issues on the analytical instrument by analyzing the raw data from the analytical instrument. The diagnostic tool accesses the analytical raw data from the control system 1 which are stored in the data storage and it is up to the user to set filters and to define what to plot. As an example, triple stage quadrupole mass spectrometers are used as detector devices 23 and biological samples are analyzed. After a certain time the ion path of the detector device 23 becomes dirty and needs to be cleaned. By plotting the peak area from the internal standard versus injection it is very easy to identify this issue if the peak area is decreasing over time. Or another example, for diagnosis of a HPLC pump the retention time versus injection is plotted wherein the stability of retention time over time is an excellent indicator of the state of the pumps.

Further, the control system 1 also comprises a laboratory notebook tool to support the use of paper notebooks. In some case, it is mandatory that work is recorded into an official paper laboratory notebook. As the necessary data are stored in the data storage 11 and data input is done using the interface unit where notebooks can be registered, entries into those notebooks and keywords linked to the entries can be performed. All this information stored in the data storage 11 is searchable by the laboratory notebook tool. With the same interface the summary sheet for the paper notebook can be generated, as the cross-reference or index with all the keywords. This can help to quickly and accurately complete the paper notebook for archiving. Furthermore, any analytical run can be linked to notebook entries of the laboratory notebook tool by selecting the notebook ID and the page for the entry. With the control system 1 it is possible to generate and print the paper report corresponding to the analytical run. This report is ready to be pasted into the paper notebook. The keywords from the analysis like compound IDs or project names are also automatically attached to the entries in the data storage 11 and are searchable.

The centralising and unifying control system 1 provides a plurality of advantageous synergy effects. For example, data mining is made available with all the information and data being stored in the data storage 11. The data format is standardized and with this unified data from different aspects of the laboratory, data mining may be performed enabling the user to learn from the stored data. The statistic interface and the diagnostic tool are data mining tools with a user interface designed to address specific questions. This data mining concept can be extended to any new ideas with the limitation that the target data are properly captured. By accessing directly the data storage 11, any query can be performed to get the needed report. In some cases, due to the recurrence of the search it is helpful to create a specific user interface to support the user. As example, prediction for chromatographic conditions such as gradient profile, columns, mobile phase and the like based on historical data from similar compounds can be needed. With this it can, e.g., be possible that usable chromatographic conditions are predicted for most of the compounds to be analysed or cases.

The following applies to the rest of this description. If, in order to clarify the drawings, a figure contains reference signs which are not explained in the directly associated part of the description, then it is referred to previous description sections.

Figure 2:
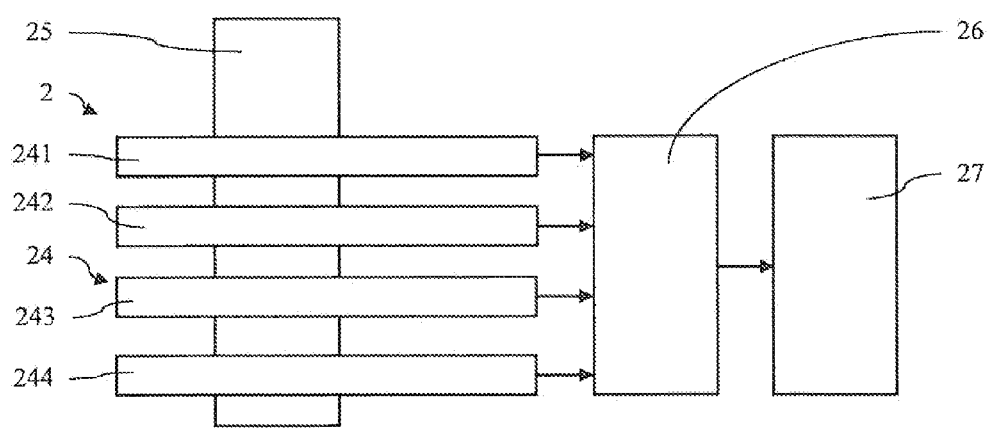
FIG. 2 shows a schematic view of an analytical instrument for multiplexing high performance liquid chromatography (HPLC)

In FIG. 2 an analytical instrument for multiplexing high performance liquid chromatography (HPLC) is shown. The analytical instrument is composed of a plurality of devices 2 comprising a sample injection device 25, a plurality of separation devices 24, a selection device 26 and a detection device 27. The plurality of separation devices 24 comprises a first separation device 241, a second separation device 242, a third separation device 243 and further separation devices 244. The sample injection device 25, e.g., can be an autosampler and particularly a HPLC-autosampler such as the autosamplers of the company CTC analytics marked "HTS PAL", of the company Shimadzu or of the company VWR marked "LaChrom L-2300". The separation devices 24 can, e.g., be a degasser, a HPLC-pump and a HPLC-column or a gas, a gas chromatography oven and a gas chromatography column or the like. The selection device 26 can be a four column selector such as article no. C5F-0004EMT of the company VICI AG. The detection device 27 can be a ultra violet absorption detector, a fluorescence detector, a mass spectrometer detector, a flame ionization detector (FID) or the like.

In some cases multiplexing HPLC can be of interest such as, e.g., if the detection device 27 purchasing cost represent around 80% of the total costs of the analytical instrument considering one work line, i.e. one gradient pump, one sampler, one column and one detector. Therefore, the control system 1 is arranged to provide multiplexing. The utilization of the HPLC analytical instrument can be multiplied closely by a factor two if on two work lines is worked in parallel. The principle underlying multiplexing HPLC is to inject alternatively samples on the two or more work lines. To use the non productive equilibration time from the column in one line a sample on a other line can be analyzed. This is physically possible by adding one ore more gradient pump, one or more injection device, one or more column and one or more divert valve. This doubles or multiplies the capacity of the analytical instrument and reduces the need for multiple systems which reduces total laboratory equipment costs. As shown in FIG. 2, multiplexing HPLC can be extended to more than two work lines with the additional benefit of gaining method diversity flexibility. Work lines can particularly be dedicated to specific methods which allows to analyse within the same analytical sequence sample needing different columns for example.

Since multiplexing HPLC can become complex in operation and handling, the control system 1 crucially improves usability of the process or making it even possible at all. Within the control system, the user defines the injection order for the samples and the work lines on which the samples have to be analyzed. The control system 1 procedures retrieves all required information to perform the analytical run such as pump method (gradient), injection method, detection method (analytical trace) and the like. The increased complexity from multiplexed instrument is reduced by the control system 1 to a usable level for routine work.

Figure 3:
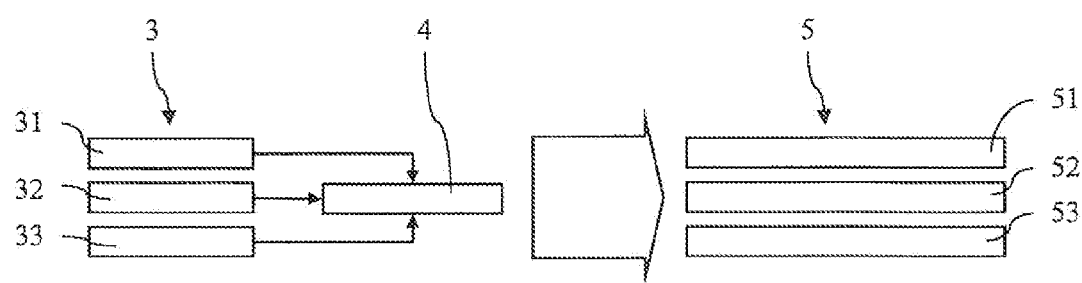
FIG. 3 shows a schematic view of sample cocktail analytics within high performance liquid chromatography (HPLC).

FIG. 3 shows sample cocktail analytics within HPLC wherein a plurality of source samples 3 such as a first source sample 31, a second source sample 32 and further source samples 33 are mixed to a analytical sample 4. The analytical sample 4 is then analysed and result concentrations 5, i.e. a first concentration 51 from the first source sample 31, a second concentration 52 from the second source sample 32 and further concentrations 53 from the further source samples 33 are provided.

Today, sample cocktail analytics is often not applied within HPLC because the time gain is often lower than the additional time needed the preparing the sample cocktail analysis. Within the control system 1 providing means for performing sample cocktail analysis this is no longer true. In particular, by means of the control system 1 sample cocktail analytics can be applied as follows. Target compounds from the different source samples 3 intended to be mixed have to be different and the detection trace from each of them has to be specific. This means that in fact not all samples can be mixed but the chromatographic conditions for mixed compounds have to be compatible such as same columns, same mobile phase and same gradient. Further, the method has to be sensitive enough to allow a dilution step from the sample cocktail preparation. If all these criteria are fulfilled then the samples can be mixed and analyzed with a detection method containing the traces from all compounds. During the data evaluation process the measured result has to be reallocated to the corresponding source sample and the final result has to be corrected by applying the right dilution factor resulting from the mixing during sample cocktail preparation.

The automatic preparation of the mixed compound and of the results by the control system 1 allows to conveniently apply sample cocktail analytics. Thereby, analysis time can essentially be reduced which is devised by the number of mixed samples. Furthermore, by having access to the relevant information from the data storage, a procedure can be generated within the control system 1 supporting the user in sample cocktail analysis. The control system 1 analyzes the methods for sample cocktail compatibility for all the compounds to analyze within one run. This method analysis follows some simple rules like minimum required mass difference for the parent. The columns, the mobile phase and the gradient profile have to be identical. Depending on the compound sensitivity allow sample cocktail of three compounds if high, two compounds if medium of and no sample cocktail if the sensitivity is low. Further, this procedure comprises making some sample cocktail proposal according to the previously defined rules and creating the virtual processing sample container where the source samples 3 are mixed if the user accepts the previous sample cocktail proposal. Using the accordingly arranged sample modelling unit 13 the real sample cocktail samples can be prepared in an automatic way. The analysis can be performed as usual and the application of the dilution factor is done automatically by the control system 1.

In an example of an analysis scenario, i.e. an exemplary application of the control system 1, if a set of samples is received by a laboratory in which different compounds have to be quantified. Sample information data are all captured in a laboratory information management system (LIMS). The analytical activities start with the import of the compound list into the control system. The checks for existing methods as for flags are launched. For the compounds where no existing methods were found, the method development can start and for the others the methods are ready to use. When the full set of methods is developed, tested and finalized the work can continue in the control system 1. The information about the sample is imported into the data storage 11. The sample cocktail procedure is launched, if the sample cocktail proposal is accepted the work list for the pipetting robot is exported. The samples to analyze are placed on the pipetting robot with the needed reagents for the sample workup. The robot program is launched with the exported work list as instruction file. During the time the robot prepares the analytical samples, the user checks the instrument status with the control system and then he does what has to be done on the instrument such as change filter, clean ion source from the detector, fill the mobiles phases and the like.

Then, samples and instrument are ready and in the control system 1 the analytical sequence can be finalized with or without the multiplexing option. The work lists for the instrument are exported, the analytical samples are placed on the analytical instrument and the analysis is started. When the analytical run is completed the raw data can be processed with the native software of the detector. Chromatogram integrations are reviewed by the user and if the result quality is as expected the data are imported into the control system 1. During the import procedure dilution factor and average calculation is automatically applied. After a last check by the user, the analysis is finalized and locked. If the analysis has to be documented in a laboratory notebook, the link to the notebook reference is made in the control system 1 and the report is printed and pasted into the laboratory notebook. A report can be exported and send to the customer or the final results can be upload to a LIMS. To make an optimal use of the time, the samples are analyzed overnight and during the day the user has time to finalize the analysis from the previous day, prepare the new analysis, and to maintain the instrument.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figs. individually although they may not have been described in the afore or following description. Also, alternatives of the embodiments described in the figures and the description and single alternatives of features thereof can be disclaimed from the subject matter of the invention.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. A computer program may be stored/distributed on a suitable medium, such as an optical storage medium or a solid-state medium supplied together with or as part of other hardware, but may also be distributed in other forms, such as via the Internet or other wired or wireless telecommunication systems. In particular, e.g., a computer program can be a computer program product stored on a computer readable medium which computer program product can have computer executable program code adapted to be executed to implement a specific method such as the method according to the invention. Any reference signs in the claims should not be construed as limiting the scope.

The invention claimed is:

1. A computerized control system (1) for automatically controlling a plurality of devices (2) configured to perform steps of a separation and detection process for quantitative sample analysis of pharmaceutical samples, said control system comprising:
   a computer data storage unit (11),
   a computerized device modelling unit (12),
   a computerized sample modelling unit (13),
   a plurality of devices configured to perform separation and detection process for quantitative pharmaceutical sample analysis,
   a pipetting robot,
   a computerized sequence generating unit (14) and
   a computerized interface unit (16), wherein:
the computer data storage unit (11) is configured to receive and store characteristic data of each of the devices (2) and to store data of source samples (3), said data of source samples comprising compound data;
the device modelling unit (12) is configured to model the devices (2) using the characteristic data of the devices (2)

stored in the data storage unit (11) said modeling being performed by receiving, storing data related to the devices (2), defining analytic instrument work lines with default parameters to be implemented in the devices (2);

the sample modelling unit (13) is configured to virtually create analytical samples and to generate work lists to control the pipetting robot that generates a plurality of analytical samples to be analysed in the separation and detection process for quantitative sample analysis using the data of source samples (3) held in the data storage (11);

the sequence generating unit (14) is configured to:
define an analytical sample sequence of the analytical samples within the separation and detection process for quantitative sample analysis that are to be implemented by utilization of the devices (2) said analytical sample sequence being then sent to the interface unit (16); and
the interface unit (16) is configured to operate the devices (2) of the separation and detection process for quantitative sample analysis in accordance with the analytical sample sequence defined by and received from the sequence generating unit (14).

2. The control system (1) according to claim 1, comprising a method modelling unit (15) wherein the data storage unit (11) is configured to hold data of methods for the separation and detection process for quantitative sample analysis, the method modelling unit (15) is configured to provide a method for the separation and detection process for quantitative sample analysis in accordance with the analytical sample sequence defined by the sequence generating unit (14) using the methods data held in the data storage (11), and the interface unit (16) is configured to operate the devices (2) of the separation and detection process for quantitative sample analysis in accordance with the method provided by the method modelling unit (15).

3. The control system (1) according to claim 2, wherein the data storage unit (11) is configured to hold data of compounds of the source samples (3) and the method modelling unit (15) is configured to evaluate the method to be implemented within the separation and detection process for quantitative sample analysis for each of the compounds of the source samples (3).

4. The control system (1) according to claim 3, wherein the method modelling unit (15) is configured to provide a presentation of methods and to detect a selection of the method to be implemented in the system.

5. The control system (1) according to claim 2, wherein the method modelling unit (15) is configured to evaluate a failed method within the separation and detection process for quantitative sample analysis for the compounds of the source samples (3).

6. The control system (1) according claim 1, further storing interface format data of a control software of at least one of the devices (2) wherein the interface unit (16) is configured to communicate with the control software of the at least one of the devices (2) in order to operate the at least one of the devices (2) within the separation and detection process for quantitative sample analysis in accordance with the analytical sample sequence defined by the sequence generating unit (14) using the interface format data.

7. The control system (1) according to claim 6, wherein the interface unit (16) is configured to communicate with the control software of the at least one of the devices (2) by generating files which are importable by the control software of the at least one of the devices.

8. The control system (1) according to claim 1, comprising a computerized robot unit configured to control a robot said robot comprising means for transferring volumes within a plurality of source samples (3) held in containers into the analytical samples (4) said source samples having been generated by the sample modelling unit (13) and located in processing sample containers in accordance with the analytical sample sequence defined by the sequence generating unit (14).

9. The control system (1) according to claim 8, wherein the robot unit is configured to apply volume transfer within transformation of the source samples (3) into the analytical samples (4).

10. The control system (1) according to claim 1, wherein the devices (2) of the separation and detection process for quantitative sample analysis are configured to perform multiplexing HPLC, comprising:
a first number of separation devices (24),
a second number of injection devices (25) and
a third number of detection devices (27),
wherein the first number and the second number are equal and are bigger than the third number and wherein the separation devices (24) and the injection devices (25) are configured in a plurality of lines being connected to the at least one detector device (27).

11. The control system (1) according to claim 1, wherein the sample modelling unit (13) is configured to:
evaluate the compound data of the source samples (3) according to their detection trace and the compatibility of their chromatographic preferences and
mix suitable source samples (3)
said evaluation and mix being defined and used for generating the plurality of analytical samples (4) to be analysed in the separation and detection process for quantitative sample analysis.

12. The control system (1) according to claim 1, further comprising a maintenance unit wherein the data storage (11) is arranged to hold data of each of the devices (2), said data comprising maintenance data, and the maintenance unit is configured to induce maintenance of the devices (2) taking into account the data of each of the devices.

13. The control system (1) according to claim 12, wherein the maintenance unit is configured to predefine a value of maintenance data of each of the devices, to count a trigger value associated to the maintenance data of each of the devices (2) and to provide an alert in response to the counted trigger value equaling the predefined value.

14. The control system (1) according to claim 12, wherein the maintenance unit is configured to store data of maintenance of each of the devices (2) in the data storage (11) and to provide a maintenance report for each of the devices (2).

15. The control system (1) according to claim 1, wherein the data storage unit comprises the characteristic data of each of the devices (2) and said characteristic data comprise default settings of each of the devices (2) and the sequence generating unit (14) is configured to define the analytical sample sequence of the analytical samples (4) in accordance with the default settings of each of the devices (2).

16. The control system (1) according to claim 3, wherein the method modelling unit (15) is configured to evaluate a failed method within the separation and detection process for quantitative sample analysis for the compounds of the source samples (3).

17. The control system (1) according to claim 13, wherein the maintenance unit is configured to store data of maintenance of each of the devices (2) in the data storage (11) and to provide a maintenance report for each of the devices (2).

* * * * *